United States Patent [19]
Longhini et al.

[11] Patent Number: 5,149,267
[45] Date of Patent: Sep. 22, 1992

[54] DENTAL SHADE GUIDE ASSEMBLY

[75] Inventors: Ross A. Longhini, Woodbury; Daryl L. Neisse, Lake Elmo; Gerald E. Drake, Oakdale; James R. Kvitrud, White Bear Lake, all of Minn.

[73] Assignee: Minnesota Mining and Manufacturing Company, St. Paul, Minn.

[21] Appl. No.: 647,551

[22] Filed: Jan. 29, 1991

[51] Int. Cl.$^5$ .............................................. A61C 19/10
[52] U.S. Cl. ..................................................... 433/26
[58] Field of Search ........................... 433/26, 72, 163

[56] References Cited

U.S. PATENT DOCUMENTS

| | | | |
|---|---|---|---|
| 2,262,641 | 11/1941 | Hayward | 433/26 |
| 2,765,534 | 10/1956 | Bloom et al. | 433/26 |
| 2,805,478 | 9/1957 | Adams | 433/26 |
| 3,521,357 | 7/1970 | Berglund et al. | 433/26 |
| 4,115,922 | 9/1978 | Alderman | 433/26 |
| 4,541,801 | 9/1985 | Mackert et al. | 433/26 |
| 4,793,805 | 12/1988 | Pitre | 433/26 |
| 4,802,850 | 2/1989 | Boon | 433/26 |
| 5,066,227 | 11/1991 | Pozzi | 433/26 |
| 5,078,598 | 1/1992 | Neisse | 433/26 |

OTHER PUBLICATIONS

"Suggestions for Shade Selection with your New Trubyte Bioform Extended Range Shade Guide", Dentsply Int'l 1973, 1983.
"Lumin Shade Guide", Vident.

Primary Examiner—Gene Mancene
Assistant Examiner—Cindy A. Cherichetti
Attorney, Agent, or Firm—Gary L. Griswold; Walter N. Kirn; James D. Christoff

[57] ABSTRACT

An assembly for holding dental shade guides has a first holder and a second holder, both of which include coupler parts for coupling the holders to each other and to other holders as desired in modular fashion. Each holder may be connected to the adjacent holder in one of two possible orientations in order to bring different shade guides into closer view. Additionally, the shade guides are releasably connected to the holders and may be inserted in receptacles of the holders in a variety of orientations.

18 Claims, 2 Drawing Sheets

DENTAL SHADE GUIDE ASSEMBLY

BACKGROUND OF THE INVENTION

1. Field of the Invention

This invention relates to an assembly for holding a number of dental shade guides.

2. Description of the Related Art

Weakened, damaged or missing teeth are repaired by dental restorations Some restorations are made by using a dental composite material that repairs and sometimes replaces damaged tooth structure. Other restorations such as crowns, bridges, implants, dentures and the like are made of an artificial tooth or set of teeth that is secured in place in the oral cavity.

Dentists use dental shade guides to select an appropriate color for restorations. Typically, a set of dental shade guides is used, each of a different color. The shade guides are held next to the teeth in order to facilitate selection of the shade guide having a color which best matches the color of the patient's teeth. Once a particular guide is chosen, indicia on the guide enable the dentist to choose restorative material with proper coloring or pigments.

Certain conventional shade guides are molded in the shape of a tooth, and have a depending handle for holding the guide next to the patient's teeth. A wire or chain-like member is threaded through holes in the handles of a number of shade guides in order to retain the shade guides together and yet permit grasping of individual shade guides as desired However, both hands are normally needed when attempting to compare the color of one shade guide to the color of another shade guide.

Other shade guide assemblies include a holder having a number of receptacles arranged in a row. Each receptacle is adapted to releasably receive a shade guide in such a manner that a portion of the shade guide extends above the holder and is visible. The dentist can use one hand to support the holder next to the patient's teeth to observe a number of shade guides at the same time (and, if desired, remove one or more of the guides from the holder for better viewing). However, only a limited number of shade guides can fit in the holder. While a larger holder with additional receptacles could be provided, such an arrangement might not be entirely satisfactory in instances where a larger holder would be cumbersome or in instances where many of the shade guides would not be needed during the selection process.

SUMMARY OF THE INVENTION

The present invention concerns a dental shade guide assembly that has a first holder with a number of dental shade guides arranged in a row, and a second holder having a number of shade guides arranged in a row. A coupler releasably couples the first holder to the second holder, and sustains the first holder in a certain orientation relative to the second holder when the first holder is coupled to the second holder such that said row of shade guides of said first holder is generally parallel with said row of shade guides of said second holder.

As such, the assembly is modular in nature and can be made larger or smaller as the need arises. When a smaller assembly or the use of fewer shade guides is desired, one of the holders can be detached from the rest of the assembly for ease of use and manipulation. Further, the detached holder can easily be reconnected with the assembly as needed. The coupler ensures that the holders are sustained in a certain orientation relative to each other so that the dental shade guides of both holders when coupled together remain in properly positioned rows and can be easily viewed.

DETAILED DESCRIPTION OF THE PREFERRED EMBODIMENT

Figure 1:
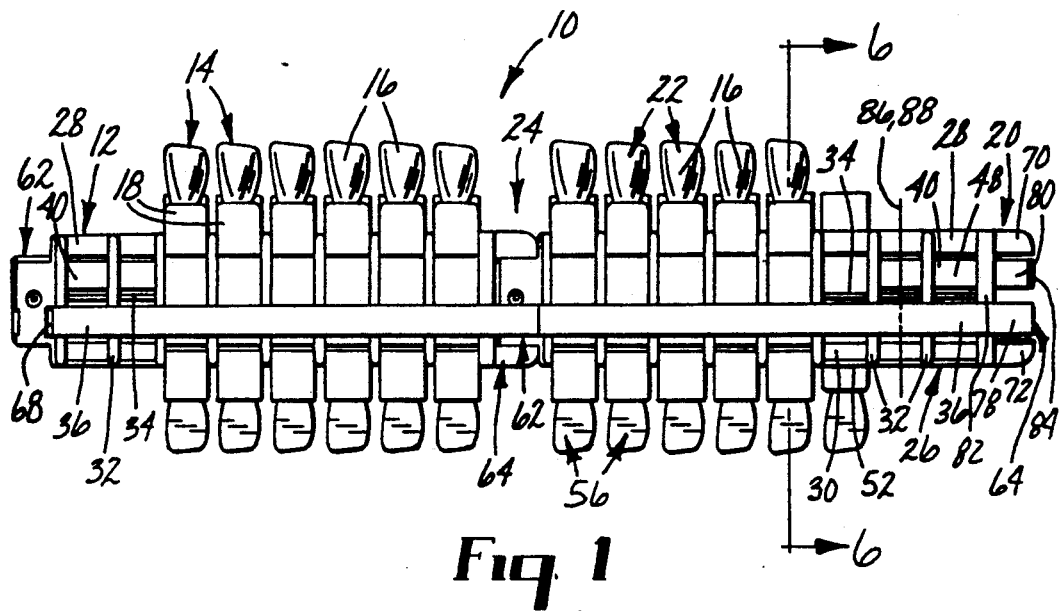
FIG. 1 is a side elevational view of an assembly in accordance with the present invention, illustrating a first holder and a second holder coupled together by a coupler.

A dental shade guide assembly 10 is illustrated in FIG. 1 and includes a first holder 12 having a number of dental shade guides 14 arranged in a straight row. A second holder 20 has a number of shade guides 22 that are also arranged in a straight row. A coupler 24 releasably couples the first holder 12 to the second holder 20, and sustains the first holder 12 and the row of shade guides 14 in an aligned, parallel orientation relative to the second holder 20 and the row of shade guides 22 when the first holder 12 is coupled to the second holder 20.

Each of the shade guides 14, 22 has a tooth-shaped first portion 16 and an elongated, bar-shaped second portion 18 with a thickness that varies along its length. The shade guides 14, 22 are integrally molded of a synthetic resinous material, and various pigments are added so that each shade guide 14, 22 has one of a number of different colors that each matches a color or shade of available restorative material. Additional information regarding the shade guides is disclosed U.S. Pat. No. 5,078,598, filed Aug. 10, 1990.

FIGS. 2-4 and 6 illustrate the second holder 20 detached from the first holder 12. The first holder 12 is constructed identical to the second holder 20 and consequently the following description of the second holder 20 is also applicable to the first holder 12.

The second holder 20 includes a body 26 (FIGS. 4–6) preferably integrally molded of a synthetic resinous material such as polycarbonate or polyester (for example, polybutyleneterephthalate). The body 26 includes a top elongated beam 28 and a bottom elongated beam 30 that are interconnected by a spaced series of parallel, upright ribs 32. A central strut 34 interconnects the ribs 32 and extends in parallel relation to the beams 28, 30.

The body 26 also has an elongated bar 36 that extends across and is attached to each rib 32 along a front or first side 38 (see FIG. 6) of the holder 20. A second bar 40 extends across and is attached to an opposite side of the ribs 32 along a back or second side 42 of the holder 20. The bars 36, 40 and beams 28, 30 are parallel to a central longitudinal axis 44 (FIGS. 1 and 4) of the second holder 20.

The shade guides 22 are received in respective receptacles 48 formed in the body 26 between adjacent pairs of ribs 32. As can be appreciated by comparing FIGS. 4, 5 and 6, each receptacle 48 has an inner side defined by the sides of the beams 28, 30 and the edge of the strut 34. The outer side of each receptacle 48 is defined by the inner side of the bar 36 that straddles the ribs 32.

Figure 6:
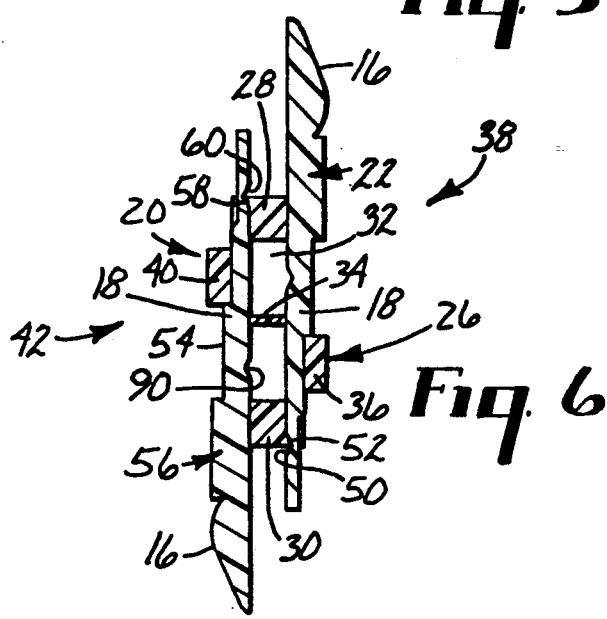
FIG. 6 is an enlarged cross-sectional view taken along lines 6—6 of FIG. 1.

As shown in FIG. 6, the shade guide 22 has a groove 50 that extends transversely across a rear, lower side of the bar-shaped second portion 18. When the shade guide 22 is inserted in the receptacle 48, the groove 50 engages a projecting lip 52 that is formed on the lower edge of the bottom beam 30 between each adjacent pair of ribs 32. The shade guide 22 is somewhat flexible and bends slightly when inserted into the receptacle 48 to enable the groove 50 to snap over the lip 52. The lips 52 function as a retention means for releasably retaining the shade guides 22 in respective receptacles 48.

The body 26 is an essentially mirror-image structure when viewed at intervals 180 degrees apart about the axis 44. As such, a second row of receptacles 54 (FIGS. 5 and 6) are formed along the second side 42 of the holder 20 for receiving a straight row of dental shade guides 56 in opposite relation to the guides 22 as illustrated in FIG. 6. To this end, the top beam 28 also has a lip 58, (FIG. 6) similar to lip 52 for engaging a groove 60 formed in the backside of the shade guides 56.

Figure 4:
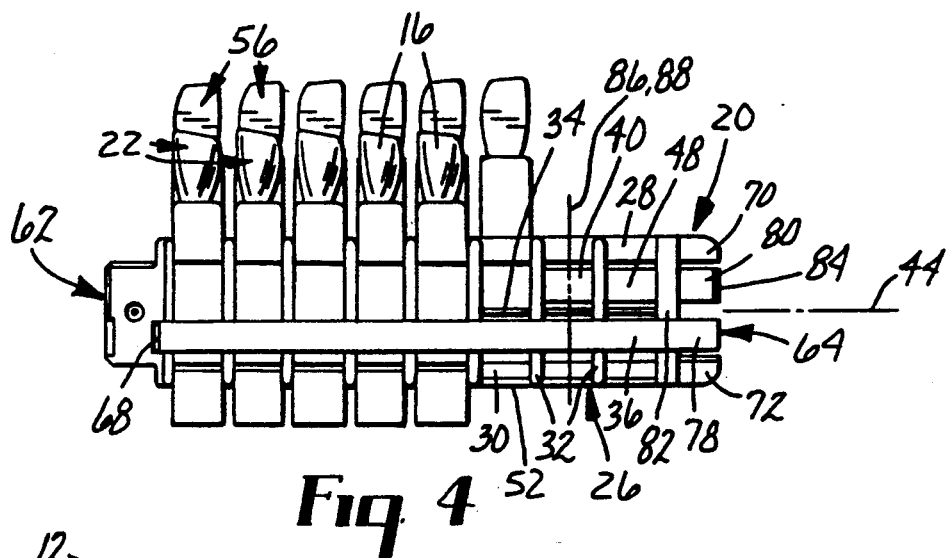
FIG. 4 is a view somewhat similar to FIG. 3 except that the shade guides are shown in yet another orientation.
Figure 5:
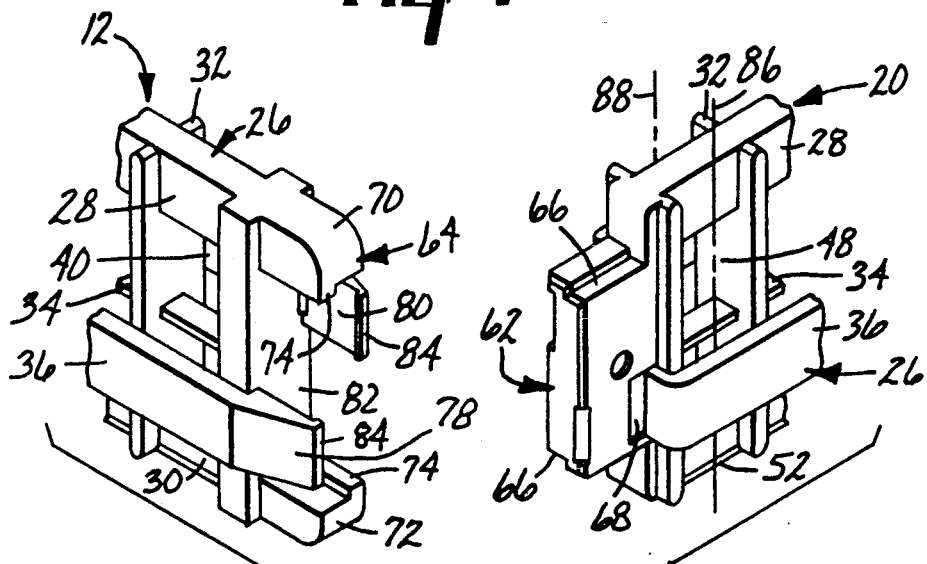
FIG. 5 is an enlarged, perspective view of the coupler shown in FIG. 1 with parts of the coupler illustrated in an uncoupled orientation.

The coupler 24 includes a male second part 62 that is integrally coupled to a left end of the second holder 20 (viewing FIGS. 1-5), and a female first part 64 that is integral with the right end of the first holder 12 (viewing FIGS. 1 and 5). The male part 62 comprises a short, somewhat rectangular block that projects outwardly from the endmost rib 32 in the direction of the axis 44. The top and bottom of the part 62 have a stepped-like keyway 66 (FIG. 5), and opposite sides of the part 62 have a recess 68 (only one
  shown in FIG. 5) that lies next to the terminus of the corresponding bar 36, 40.

As can be understood, the recess 68 provides a means for releasably coupling the male part 62 to the female part 64 in snap-fit relation as the male part 62 moves toward the female part 64.

The female part 64 includes extensions 70, 72 of the top and bottom beams 28, 30, respectively. The extensions 70, 72 have elongated flanges 74 that matingly slide in respective keyways 66 when the coupler parts 62, 64 are brought together in a direction along axis 44. The flanges 74 provide stability to the coupler 24 by resisting relative rotation of the holders 12, 20 about the axis 44.

The female part 64 also includes terminal ends 78, 80 of the bars 36, 40 respectively. The ends 78, 80 extend outwardly along the axis 44 from a right end rib 82 (viewing FIGS. 4-5) that is somewhat thicker than the remaining ribs 32. Each end 78, 80 has an inwardly extending lug 84 complemental in size to the recesses 68 formed in the male part 62.

When the holders 12, 20 are brought together in a direction along the axis 44, the flanges 74 prevent the male part 62 from advancing into the female part 64 unless the holders 12, 20 are laterally aligned along a common axis (i.e., unless the longitudinal axes 44 of the holders 12, 20 are colinear) and unless the longitudinal axes 86, 88 (see FIGS. 1 and 5) of the receptacles 48, 54 of the first holder 12 are parallel with the longitudinal axes 86, 88 of the receptacles 48, 54 of the second holder 20. As the part 62 slides past the lugs 84, the part 62 deflects the somewhat flexible ends 78, 80 outwardly in a direction away from each other. The ends 78, 80 remain in an outwardly deflected position until the left end (viewing FIG. 5) of the part 62 is next to the rib 82, at which time the lugs 84 snap into respective recesses 68 and the ends 78, 80 return to their normal orientation.

The ends 78, 80 and the extensions 70, 72 provide stability to the assembly 10 when the first holder 12 is coupled to the second holder 20, and the lugs 84 retain the parts 62, 64 coupled together until intentionally moved apart. The coupler 24 self-sustains the holders 12, 20 in a rigid orientation relative to each other so that the user need grasp only one of the holders 12, 20 during typical use, since the coupler 24 retains the non-grasped holder when suspended in alignment with the grasped holder. Both of the holders 12, 20 are provided with male parts 62 and female parts 64 so that any number of shade guide holders may be coupled together.

The orientation of the shade guides 22, 56 when positioned in the holder 20 in the manner shown in FIGS. 1 and 6 is convenient for many users due to the symmetry of the rows of guides 22, 56 relative to the axis 44. When the holder 20 is in the position shown in FIGS. 1 and 6, the rounded, front part of the upper tooth-shaped first portion 16 (see FIG. 6) of the shade guides 22 faces the viewer for facilitating color matching. However, if the user desires to view the front of the shade guides 56, the user need only flip the holder 20 in an arc 180 degrees about the axis 44 in order to bring the row of shade guides 56 into an upright location.

Figure 2:
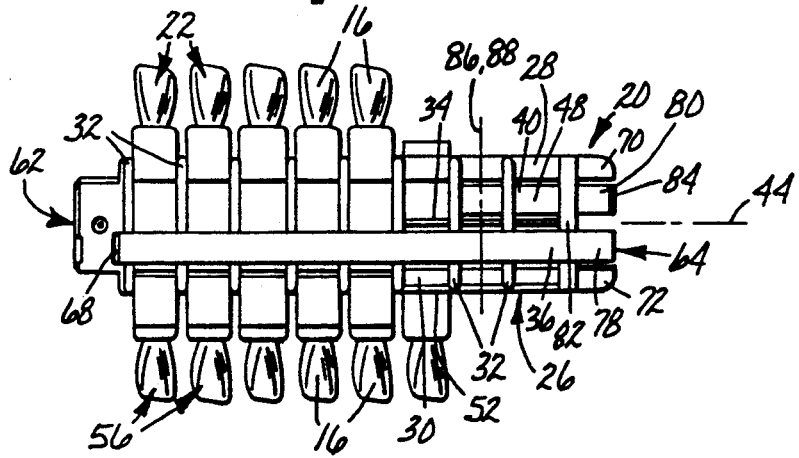
FIG. 2 is a view somewhat similar to FIG. 1 except that only the second holder is shown, and a bottom row of dental shade guides has been arranged in a somewhat different orientation.

As an alternative, FIG. 2 illustrates a somewhat different orientation of the shade guides 56 in the holder 20. In FIG. 2, each of the lower shade guides 56 was rotated about its longitudinal axis before insertion into the corresponding receptacle 54 (FIG. 6). In this manner, the curved, front face of the tooth-shaped portion 16 of the shade guides 56 faces the viewer in the same manner as the tooth-shaped portion 16 of the upper shade guides 22. Although the grooves 60 of the shade guides 56 do not engage the lips 58 in such an orientation, there is a sufficiently small clearance between the shade guides 56 and structure defining the receptacles 54 to releasably retain the shade guides 56 in the holder 20. The holder 20 is flipped end-over-end in order to view the front face of the tooth guides 56.

Figure 3:
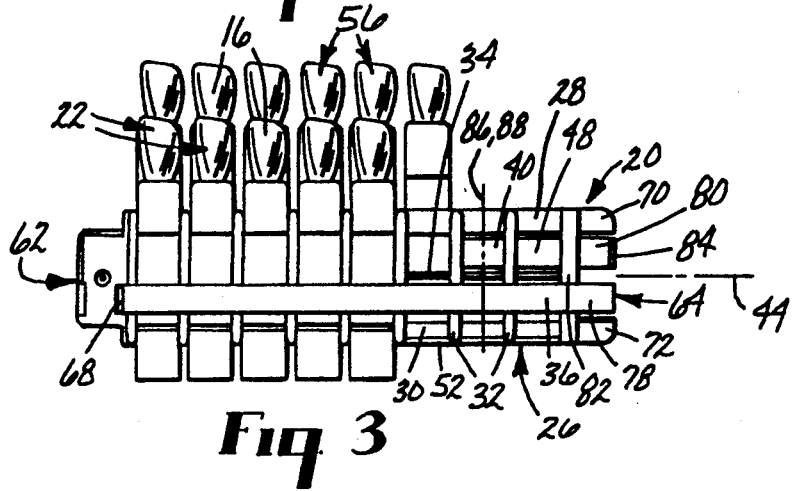
FIG. 3 is a view somewhat similar to FIG. 2 except that the bottom row of shade guides has been removed and inserted into the holder from the top.

Another alternative arrangement of the shade guides 56 is shown in FIG. 3. In this instance, the shade guides 56 have been inserted into the receptacles 54 in an opposite direction along the axis 88 (in comparison to the direction of insertion of FIGS. 1 and 2), so that all of the shade guides 22, 56 are upright and the curved face of the tooth-shaped portion 16 of each shade guide 22, 56 faces the user. The configuration shown in FIG. 3 is useful for some dentists who prefer to see all of the shade guides next to each other and eliminate the need to rotate the holder 20 about the axis 44 or flip the holder 20 end over end. The shade guides 56 in the orientation shown in FIG. 3 are releasably held by the holder 20 due to the relatively small clearance between the shade guides 56 and the holder 20, and the grooves 60 do not engage the lips 58 in such an orientation.

Another use of the holder 20 is shown in FIG. 4, where the shade guides 56 are upright and behind the shade guides 22 in the manner shown in FIG. 3, but are rotated 180 degrees about their respective longitudinal axes before insertion into corresponding receptacles 54. To view the front face of the shade guides 56, the holder is flipped end over end. A second groove 90 (FIG. 6) engages the lip 58 when the shade guide 56 is in the position shown in FIG. 4 in order to securely retain the shade guide 56 in place.

Advantageously, the body 26 is of substantially open construction and the proximal row of shade guides 22 is substantially exposed, covered from the front only by the bar 36. As such, the substantial extent of each shade guide 22 can be easily observed without removal from the holder 20. However, individual shade guides 22, 56 can readily be removed from the holder 20 when desired.

We claim:

1. A dental shade guide assembly comprising:
   a first holder having a number of dental shade guides arranged in a row;
   a second holder having a number of dental shade guides arranged in a row; and
   a coupler for releasably coupling said first holder to said second holder, said coupler including a first part connected to said first holder and a second part connected to said second holder, said first part having means for releasably coupling said first part to said second part in snap-fit relation as said first part moves toward said second part, said coupler sustaining said first holder in a certain orientation relative to said second holder when said first holder is coupled to said second holder such that said row of shade guides of said first holder is generally parallel with said row of shade guides of said second holder.

2. The assembly of claim 1, wherein said row of dental shade guides of said second holder is substantially colinear with said row of shade guides of said first holder when said first holder is coupled to said second holder.

3. The assembly of claim 1, wherein said first holder and said second holder extend along a common reference axis when said first holder is coupled to said second holder, and wherein said coupler is adapted to couple said first holder to said second holder when said second holder is oriented in either one of two different orientations relative to said first holder about said reference axis.

4. The assembly of claim 3, wherein said two different orientations are approximately 180° apart about said reference axis.

5. The assembly of claim 4, wherein said coupler couples said first holder to said second holder when said second holder is moved toward said first holder along said reference axis.

6. The assembly of claim 1, wherein said first holder includes a body, and wherein said dental shade guides of said first holder are releasably connected to said body.

7. The assembly of claim 6, wherein said body includes a number of receptacles each adapted to receive one of said number of dental shade guides of said first holder along an axis in either one of two different orientations relative to said axis.

8. The assembly of claim 1, wherein said dental shade guides of said first holder are elongated, and wherein said first holder includes a body having a number of receptacles each adapted to receive one of said number of dental shade guides of said first holder, said receptacles being substantially open along one side thereof for permitting viewing of the substantial extent of said dental shade guides.

9. A dental shade guide assembly comprising:
   a first holder having a number of dental shade guides arrange din a row;
   a second holder having a number of dental shade guides arranged in a row; and
   a coupler for releasably coupling said first holder to said second holder, said coupler sustaining said first holder in a certain orientation relative to said second holder when said first holder is coupled to said second holder such that said row of shade guides of said first holder is generally parallel with said row of shade guides of said second holder, wherein said coupler includes a female part connected to said first holder and a male part connected to said second holder, and wherein said male part coupled to said female part in snap-fit relation.

10. The assembly of claim 9, wherein said male part and said female part include stepped flanges slidably engageable with each other for substantially preventing rotation of said first holder relative to said second holder when said first holder is coupled to said second holder.

11. A dental shade guide assembly comprising:
    a holder having a first row of receptacles and a second row of receptacles arranged in side-by-side relationship with said first row; and
    a plurality of dental shade guides each received in respective receptacles of said first row and said second row, each of said receptacles having a longitudinal axis and opposite ends with openings at each end, each of said receptacles being adapted to receive a shade guide both in a first direction along said longitudinal axis and in a second direction along said longitudinal axis opposite said first direction and to releasably retain said shade guide in said receptacle when moved in said first direction into said receptacle and alternatively when moved in said second direction into said receptacle.

12. The assembly of claim 11, wherein said first row is substantially straight.

13. The assembly of claim 11, wherein each of said receptacles are adapted to receive a shade guide in either one of two orientations located in an arc extending in a plane normal to said axis.

14. The assembly of claim 13, wherein said two orientations are 180° apart.

15. A dental shade guide assembly comprising;
    a holder having a first row of receptacles and a second row of receptacles arranged in side-by-side relationship with said first row; and
    a plurality of dental shade guides each received in respective receptacles of said first row and said second row, each of said receptacles having a longitudinal axis and being adapted to receive a shade guide both in a first direction along said longitudinal axis and in a second direction along said longitudinal axis opposite said first direction,
    wherein said holder includes a body having a first side and a second side opposite said first side, and wherein said first row of receptacles extends along said first side and said second row of receptacles extends along said second side.

16. The assembly of claim 15, wherein each of said receptacles of said first row and said second row are substantially open along said first side and said second side respectively for permitting viewing of a substantial extent of said shade guides.

17. A dental shade guide assembly comprising:
   a holder having a first row of receptacles and a second row of receptacles arranged in side-by-side relationship with said first row; and
   a plurality of dental shade guides each received in respective receptacles of said first row and said second row, each of said receptacles having a longitudinal axis and being adapted to receive a shade guide both in a first direction along said longitudinal axis and in a second direction along said longitudinal axis opposite said first direction, wherein each of said shade guides includes a groove, and wherein said holder includes retention means comprising a lip for engagement with said groove.

18. A dental shade guide assembly comprising:
   a first holder having a number of dental shade guides arranged in a row;
   a second holder having a number of dental shade guides arranged in a row; and
   a releasable coupler for repeatably coupling and uncoupling said first holder to said second holder, said coupler including a first part connected to said first holder and a second part connected to said second holder, said first part having means for releasably coupling said first part to said second part such that said first holder is in a certain orientation relative to said second holder.

* * * * *

UNITED STATES PATENT AND TRADEMARK OFFICE
CERTIFICATE OF CORRECTION

PATENT NO. : 5,149,267

DATED : September 22, 1992

INVENTOR(S) : Ross A. Longhini, Daryl L. Neisse, Gerald E. Drake and James R. Kvitrud It is certified that error appears in the above-identified patent and that said Letters Patent is hereby corrected as shown below:

Col. 6, line 5, "arrange din" should be -- arranged in --.

Col. 6, line 17, "coupled" should be -- couples --.

Col. 8, line 6, "arrange din" should be -- arranged in --.

Signed and Sealed this

Ninth Day of November, 1993

*Attest:*

BRUCE LEHMAN

*Attesting Officer*   *Commissioner of Patents and Trademarks*